United States Patent
Boesten et al.

(10) Patent No.: US 6,794,542 B2
(45) Date of Patent: Sep. 21, 2004

(54) METHOD FOR THE PREPARATION OF ENANTIOMERICALLY ENRICHED COMPOUNDS

(75) Inventors: Wilhelmus Hubertus Joseph Boesten, Sittard (NL); Harold Monro Moody, Maastricht (NL); Bernardus Kaptein, Sittard (NL); Johannes Paulus Gerardus Seerden, Groningen (NL); Marcelles Van Der Sluis, Groningen (NL); Ben Lange De, Munstergeleen (NL); Quirinus Bernardus Broxterman, Munstergeleen (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 10/148,853
(22) PCT Filed: Dec. 4, 2000
(86) PCT No.: PCT/NL00/00892
  § 371 (c)(1),
  (2), (4) Date: Oct. 9, 2002
(87) PCT Pub. No.: WO01/42173
  PCT Pub. Date: Jun. 14, 2001

(65) Prior Publication Data
  US 2003/0097005 A1 May 22, 2003

(30) Foreign Application Priority Data
  Dec. 8, 1999 (NL) .............................. 1013789
  Feb. 11, 2000 (NL) .............................. 1014365

(51) Int. Cl.$^7$ .......................................... C07C 233/05
(52) U.S. Cl. ...................... 564/164; 564/468; 564/488; 564/490; 558/392; 558/393
(58) Field of Search .................................. 564/164, 468, 564/488, 490; 558/392, 393; 560/42, 169

(56) References Cited

FOREIGN PATENT DOCUMENTS

| DE | 22 00 788 | 7/1973 |
| JP | 51 108002 | 9/1976 |
| WO | WO 98/02410 | 1/1998 |
| WO | WO 99/47489 | 9/1999 |

OTHER PUBLICATIONS

Marshall and Garofalo. "Oxidative Cleavage of Mono–, Di–, and Trisubstituted Olefins to Methyl Esters through Ozonolysis in Methanolic NaOH" J. Org. Chem. 58–3675–3680 (1993).

Primary Examiner—Shailendra Kumar
(74) Attorney, Agent, or Firm—Morrison & Foerster LLP

(57) ABSTRACT

Process for the preparation of a diasteromerically enriched phenylglycine amide derivative in which an enantiomerically enriched phenylglycine amide is converted into the corresponding Schiff base with the aid of compound $R_2$—C(O)—$R_3$, and the Schiff base obtained is subsequently converted into the diastereomerically enriched phenyglycine amide derivative with the aid of a cyanide source, a reducing agent or an allyl organometallic compound. The phenylglycine amide derivatives obtained are interesting starting materials for the preparation of for example enantiomerically enriched α- and or β-amino acids and derivatives thereof, such as amides and esters, and amines.

16 Claims, 4 Drawing Sheets

METHOD FOR THE PREPARATION OF ENANTIOMERICALLY ENRICHED COMPOUNDS

This application is a 371 of PCT/NL00/00892, filed on Dec. 4, 2000.

The invention relates to a process for the preparation of a diastereomerically enriched compound having formula 1

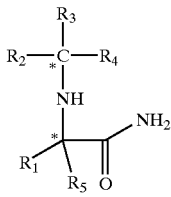
(1)

where
- $R_1$ is a substituted or unsubstituted phenyl group,
- $R_2$, $R_3$ and $R_4$ each differ from one another and $R_2$ and $R_3$ represent H, a substituted or unsubstituted (cyclo)alkyl group, (cyclo)alkenyl group, aryl group, cyclic or acyclic heteroalkyl group or heteroaryl group with one or more N, O or S atoms, or $(CH_2)_n$—$COR_6$, where n=0, 1, 2 ... 6 and $R_6$=OH, a substituted or unsubstituted alkyl group, aryl group, alkoxy group or amino group and
- $R_4$=CN, H or a substituted or unsubstituted allyl group and
- $R_5$ is H or alkyl with 1–6 C atoms, in which an enantiomerically enriched phenylglycine amide having formula 2

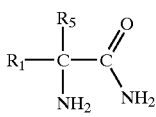
(2)

where $R_1$ and $R_5$ have the aforementioned meanings, is, with the aid of a compound having formula 3

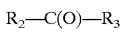
(3)

$R_2$—C(O)—$R_3$ where $R_2$ and $R_3$ have the aforementioned meanings, converted into the corresponding Schiff base or the tautomeric enamine, and the Schiff base obtained is subsequently converted into the diastereomerically enriched compound having formula 1 with the aid of a cyanide source, for instance HCN or an alkali cyanide, a reducing agent (for example $H_2$) or an allyl organometallic compound (as shown in FIG. 1, wherein R represents a substituted or an unsubstituted allyl group).

In this process an enantiomerically enriched phenylglycine amide is used as a chiral auxiliary in diastereoselective reaction concepts. The literature refers to a number of examples of processes in which chiral auxiliaries are used, for example enantiomerically enriched α-phenylglycinol or enantiomerically enriched α-methylbenzyl amine.

A drawback of the known chiral auxiliaries is that they are very costly and thus less suitable for commercial use, as the chiral auxiliaries are consumed during the process.

The applicant has now found that phenylglycine amides according to formula (2), for example phenylglycine amide, p-hydroxyphenylglycine amide or α-methylphenylglycine amide, are particularly suitable for use as chiral auxiliaries in the preparation of enantiomerically enriched compounds, in particular α-amino acids, β-amino acids, or derivatives thereof and amines (e.g. as represented in FIGS. 2, 3 and 4). This is the more surprising since phenylglycine amides are known to be susceptible to racemisation. Phenylglycine amides, for example phenylglycine amide or α-methyl phenylglycine amide are available on large scale.

Another major advantage of the invention is that, in most cases, the phenylglycine amide derivatives formed in the process of the invention result in crystalline products. This means that compounds that are not completely diastereomerically pure can be purified to diastereomerically pure compounds via a simple crystallisation step. This is in contrast with the hitherto commonly used chiral auxiliaries. These often yield oils, and, therefore, cannot be diastereomerically enriched by crystallization. Consequently, these oils (derivatised or non-derivatised) are for instance separated by means of for example (chiral) chromatography.

Suitable compounds having formula (3) are for example aldehydes, ketones, ketoacids, ketoesters, ketoamides and glyoxylic acid (derivatives), in particular pivaldehyde, methyl isopropyl ketone, acetophenone, isobutyraldehyde, pyruvic acid, trimethylpyruvic acid and ethyl acetoacetate.

Diastereomerically enriched compounds that can particularly well be prepared with the process of the invention are for example compounds according to formula 1 where $R_4$=CN. It has also been found that either of the two diastereomers may crystallise preferentially, while the other one remains in solution and epimerises in situ. This means that, under the chosen conditions, regardless of the intrinsic diastereomeric excess, complete conversion into one diastereomer may occur (the intrinsic diastereomeric excess is obtained via asymmetric induction by the chiral auxiliary under homogeneous conditions).

The aminonitrile obtained may subsequently be converted, in any one of various manners known for aminonitriles (FIG. 2), into amino acids, amino acid amides and amino acid esters, for example through acidic hydrolysis, basic hydrolysis, enzymatic hydrolysis or through metal-catalysed hydrolysis. A suitable embodiment is for example treatment with a strong acid at elevated temperature to form the corresponding diacid, which subsequently, after hydrogenolysis according to a known method (for example with the aid of $H_2$ and a Pd/C or $Pd(OH)_2$ catalyst), yields the corresponding amino acid.

The aminonitrile obtained may also be converted into the corresponding diamide, for example by treating it with a strong acid, which diamide subsequently, after hydrogenolysis of the auxiliary group, yields the corresponding amino acid amide. If desired, the amino acid amide may be converted, in a known manner (for example with a strong acid), into the corresponding amino acid.

Another conversion comprises for example treating the aminonitrile obtained with a strong acid in alcohols (for example with methanol) to form the corresponding monoester or diester, which subsequently, after hydrogenolysis of the auxiliary group, yields the corresponding amino acid ester. If desired, the amino acid ester may be converted by means of a known method (for example using a strong acid) into the corresponding amino acid.

Other compounds that can particularly well be prepared using the process of the invention are for example enantiomerically enriched amines. These amines can be prepared for instance through reduction of the Schiff base followed by hydrogenolysis according to a known method, for example with the aid of $H_2$ and a Pd/C or a $Pd(OH)_2$ catalyst (FIG. 3).

Reduction of the Schiff base can be effected for example with the aid of $NaBH_4$, $LiAlH_4$ or derivatives thereof (e.g. alkoxy derivatives such as $NaBH(OAc)_3$), with hydrogenation catalysts, for example Pd, Pt or Raney-Ni in combination with $H_2$ or under transfer-hydrogenation conditions. Especially Raney-Ni or Pd was found to be a suitable catalyst for hydrogenation reactions leading to high diastereoselectivities.

Amines and β-amino acid derivatives (e.g. as represented in FIGS. 3 and 4), too, may be particularly well prepared through selective addition to the Schiff base of allyl organometallic compounds. Particularly suitable allyl organometal compounds were found to be for example Zn or Mg, preferably Zn, derivatives. After addition of a substituted or unsubstituted allyl organometal compound to the Schiff base, the allyl compound obtained can for example be converted into a β-amino acid or a derivate thereof. A suitable embodiment is for example conversion of the double bond according to known oxidative methods, for example by catalytic oxidation, stoichiometric oxidizing agents or via ozonolysis, followed by oxidative treatment and subsequent hydrogenolysis into the corresponding β-amino acid (FIG. 4), or β-amino acid ester.

Particularly suitable appeared to be the conversion via ozonolysis in the presence of a base, for instance NaOH, and an alcohol, for example methanol, of the double bond into a β-amino acid ester derivative via a method as described in J. Org. Chem., 1993, 58, 3675–3680, and the subsequent hydrogenolysis into the corresponding β-amino acid ester.

Furthermore it has been found that the allyl compound obtained can be converted in a 3-amino alcohol derivative, for instance by ozonolysis followed by reductive work up, for instance using $NaBH_4$. Subsequently the 3-amino alcohol can be liberated by hydrogenolysis.

Amines can be obtained through reduction of the substituted or unsubstituted allyl group followed by hydrogenolysis (FIG. 3, wherein R represents a substituted or unsubstituted allyl group and $R_4^1$ represents the hydrogenated form of R).

The compounds having formula 1, where $R_1$, $R_2$, $R_3$, $R_4$, $R_5$, are as previously defined, and the compounds with formula 1 wherein $R_1$, $R_2$, $R_3$ and $R_5$ are as previously defined and $R_4$ represents $C(R_7R_8)$—$CO_2R_{10}$ or $C(R_7R_8)$—$CHR_9OH$ with $R_7$, $R_8$ and $R_9$ are each independently an alkyl or an aryl group and $R_{10}$ represents an alkyl group, are novel compounds. The compounds preferably have a diastereomeric excess of >80%, in particular >90%, more particularly >98%. The invention also relates to such compounds. The term diastereomeric excess relates to the chiral centres designated in formula (1) by asterisks.

In addition, it was found that, because of the crystalline behaviour of the phenylglycine amide derivatives obtained as intermediates, in the case of incomplete diastereoselectivity, purification by means of a single crystallisation process often leads to >98% diastereomeric excess.

The phenylglycine derivatives obtained may be converted into the corresponding amines by means of hydrogenolysis with $H_2$ using for example a Pd catalyst.

The (hetero)alkyl groups or alkoxy groups referred to in the context of the present invention preferably have 1–20 C atoms, in particular 1–5 C atoms; the (cyclo)alkenyl groups preferably have 2–20, in particular 2–9 C atoms; and the (hetero)aryl groups 2–20, in particular 3–8 C atoms. If so desired, the (hetero)alkyl, alkoxy, alkenyl, aryl, allyl, heteroaryl or amino groups may be monosubstituted or polysubstituted with for example halogen, in particular chlorine or bromine, a hydroxy group, an alkyl or (hetero) aryl group with for example 1–10 C atoms and/or an alkoxy group or acyloxy group with for example 1–10 C atoms.

The invention will now be illustrated with reference to the examples without however being limited thereto.

EXAMPLES

Example I

Strecker Reaction with Aldehyde

Figure 1:
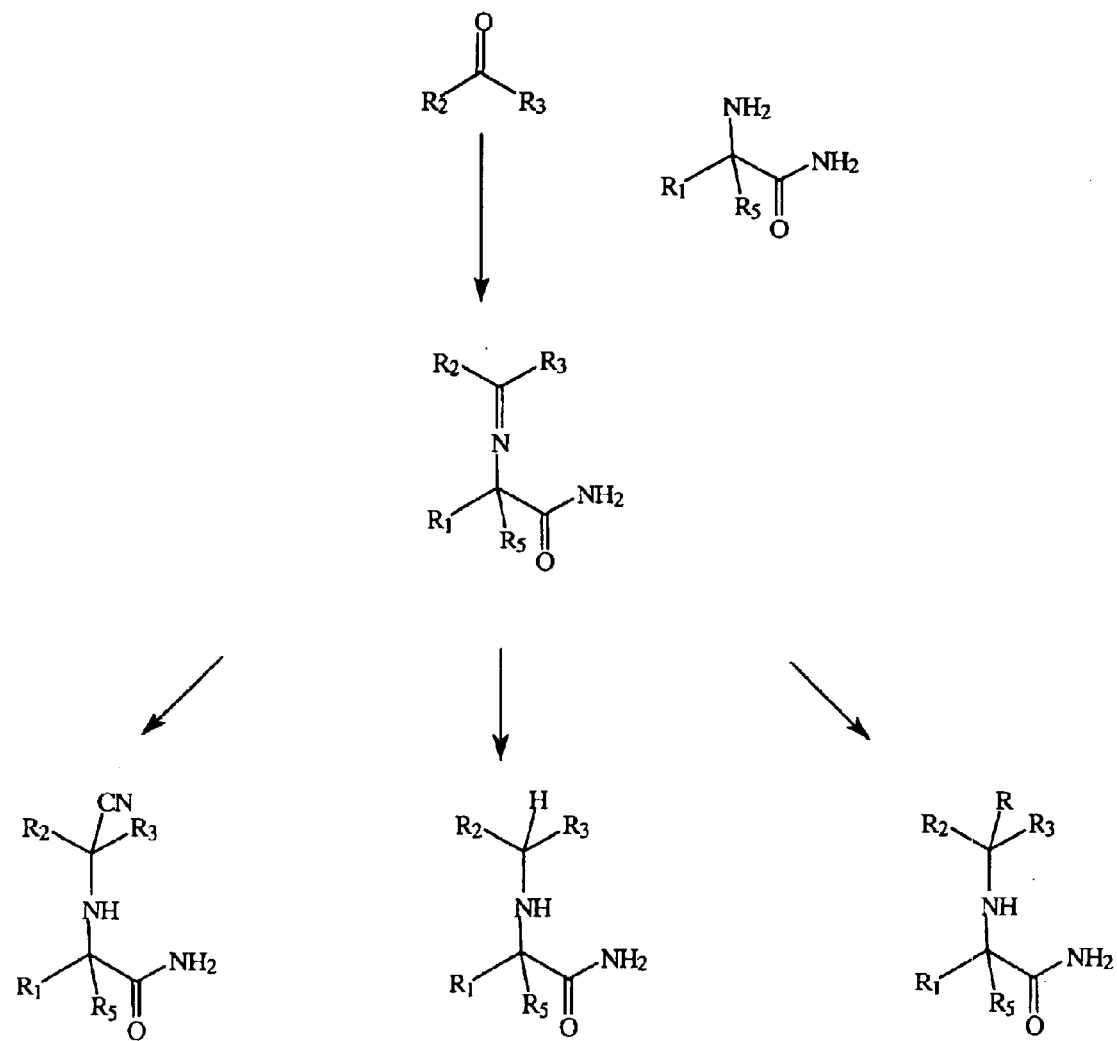
FIG. 1 illustrates the various compounds having formula (1).
Figure 2:
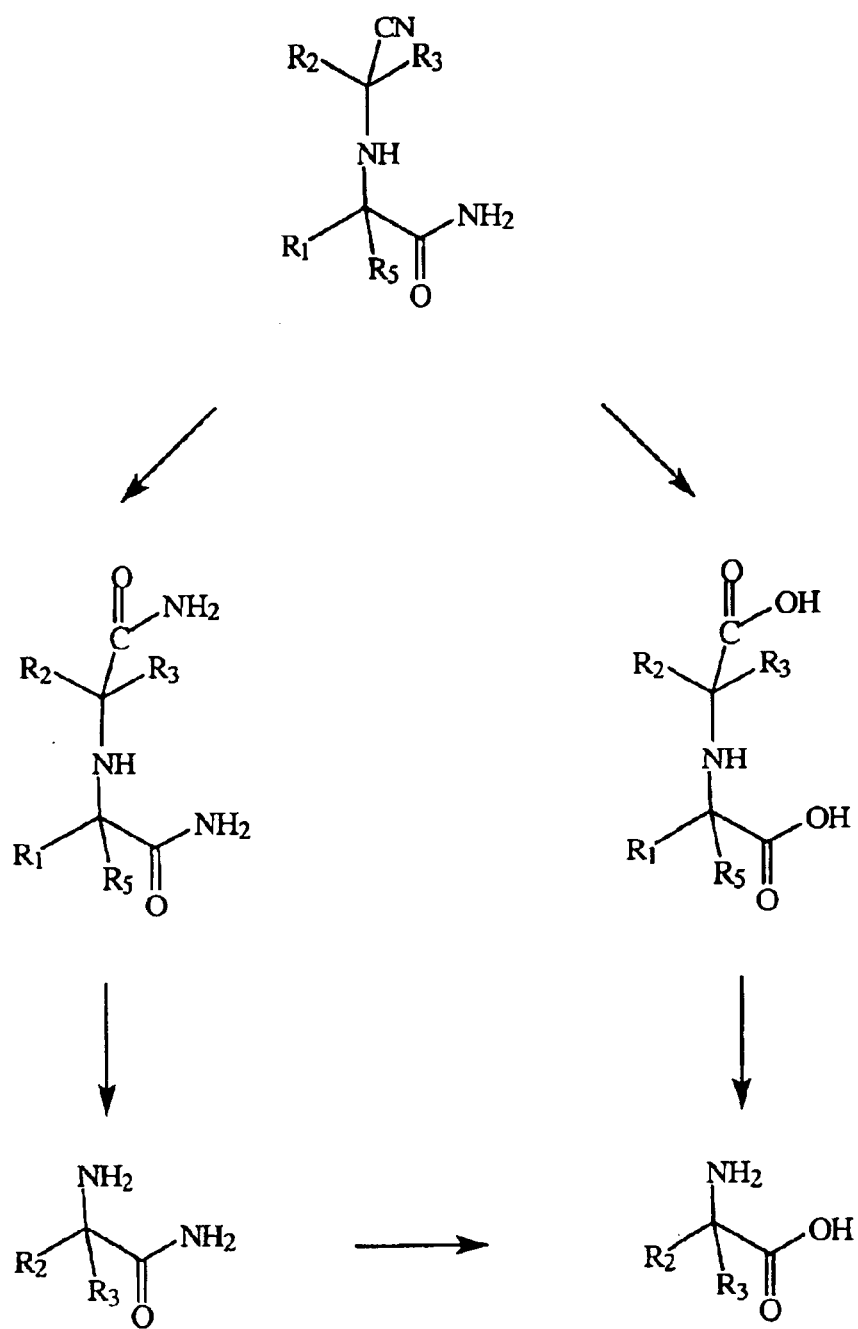
FIG. 2 illustrates general schemes for converting aminonitriles to amino acids, amides and esters.
Figure 3:
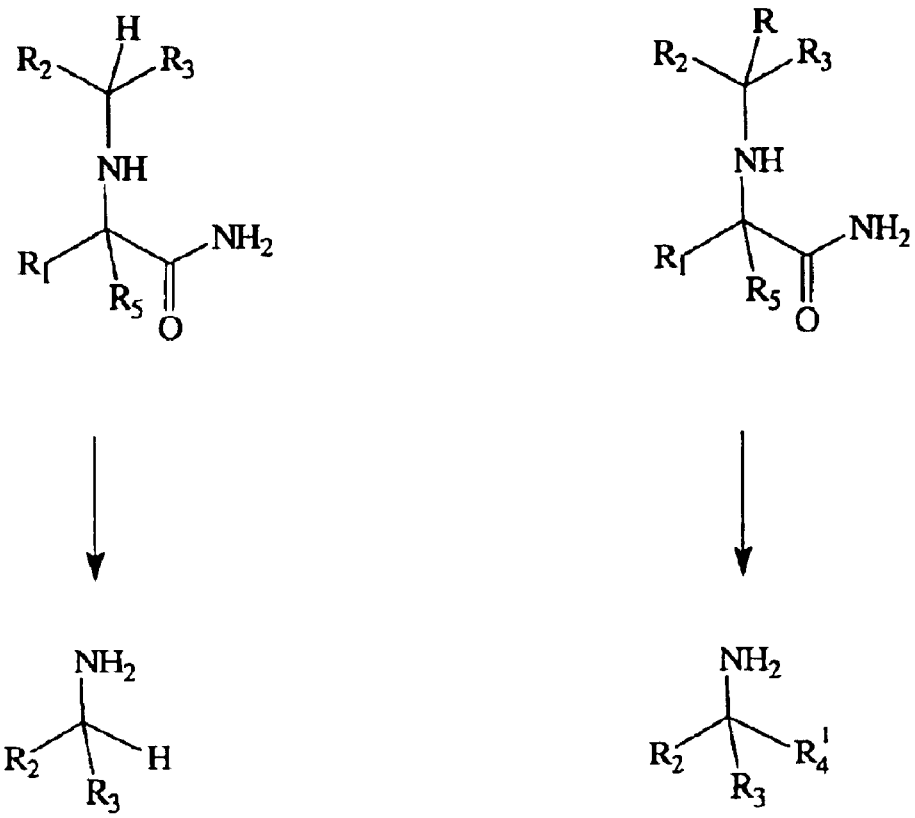
FIG. 3 illustrates a general scheme for preparing enantiomeric amines from compounds having formula (1).
Figure 4:
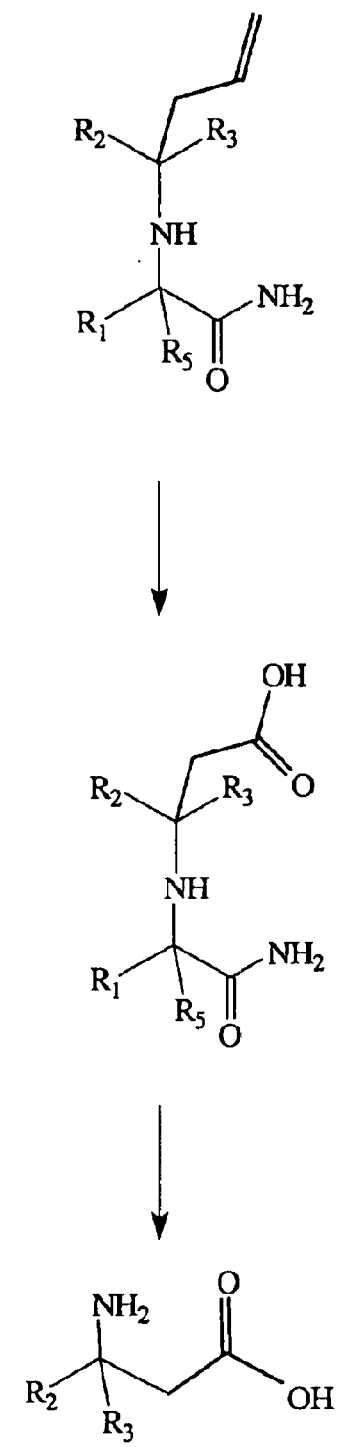
FIG. 4 illustrates a general scheme for preparing β-amino acid or acid esters from an allyl compound.

Addition of KCN to the Schiff base of (R)-phenylglycine amide and 2,2-dimethylpropanal yielding (R,S)-aminonitrile.

3.0 ml (50 mmol) of glacial acetic acid was added to 7.5 g (50 mmol) of (R)-phenylglycine amide suspended in 50 ml of water at 70° C. Next, at the same temperature, 4.3 g (50 mmol) of 2,2-dimethylpropanal and 3.25 g (50 mmol) of KCN were added. The mixture was stirred for 24 hours at a temperature of 70° C. After cooling to 30° C., the precipitate was filtered and washed with 10 ml of water.

10.4 g (42.5 mmol, 85%) of (R,S)-aminonitrile was obtained as a white solid.

Absolute configuration was determined after conversion into (S)-t-leucine. (R,S)-aminonitrile d.e. 98%, determined by $^1$H NMR analysis.

$^1$H NMR (CDCl$_3$): 0.94 (s, 9H, tBu), 2.66 (d, 1H, NH), 2.77 (d, 1H, CHCN), 4.37 (s, 1H, CHPh), 5.36 (broad s, 1H, CONH) 5.90 (broad s, 1H, CONH), 7.16–7.36 (m, 5H, Ar).

Example II

Strecker Reaction with Aldehyde

Addition of KCN to the Schiff base of (S)-phenylglycine amide and 2,2-dimethylpropanal yielding (S,R)-aminonitrile.

3.0 ml (50 mmol) of glacial acetic acid was added to 7.5 g (50 mmol) of (S)-phenylglycine amide suspended in 50 ml of water at 70° C. Next, 4.3 g (50 mmol) of 2,2-dimethylpropanal and 3.25 g (50 mmol) of KCN were added at the same temperature. The mixture was stirred for 24 hours at a temperature of 70° C. After cooling to 30° C. the solid precipitated was filtered and washed with 10 ml of water.

10.7 g (43.3 mmol, 87.3%) of (S,R)-aminonitrile was obtained as a white solid. Absolute configuration was determined after comparison with the conversion of the (S,R)-aminonitrile to (R)-t-leucine.

(S,R)-aminonitrile: d.e. 98%, determined by means of $^1$H NMR analysis.

$^1$H NMR (CDCl$_3$): 0.94 (s, 9H, tBu), 2.55 (d, 1H, NH), 2.79 (d, 1H, CHCN), 4.35 (s, 1H, CHPh), 5.34 (broad s, 1H, CONH), 5.90 (broad s, 1H, CONH), 7.10–7.38 (m, 5H, Ar).

Example III

Strecker Reaction with Ketone

Addition of NaCN to the Schiff base of (R)-phenylglycine amide and 3,4-dimethoxyphenylacetone.

To 18.6 g (100 mmol) of (R)-phenylglycine amide.HCl salt in 150 ml of MeOH and 25 ml of $H_2O$ were added, at 20–25° C., 16.5 g (100 mmol) of 30% NaCN in water and 19.3 g (100 mmol) of 3,4-dimethoxyphenylacetone. The clear solution was stirred at 20–25° C. After 82 hours the crystals that had formed were filtered and washed with 3×15 ml methanol/water (v/v 70:30).

21.6 g (61.1 mmol, 61%) of aminonitrile was obtained as a white, solid; d.e. >98%, determined by means of $^1$H NMR analysis.

$^1$H NMR (CDCl$_3$): 1.48 (s, 3H, CH$_3$), 2.60 (s, 1H, NH), 2.81 (s, 2H, CH$_2$), 3.82 (s, 3H, OCH$_3$), 3.86 (s, 3H, OCH$_3$), 4.47 (s, 1H, CHPh), 6.0 (broad s, 1H, CONH), 6.70 (broad s, 1H, CONH), 6.84–6.90 (m, 3H, Ar), 7.26–7.38 (m, 5H, Ar).

Example IV
Hydrolysis of the Aminonitrile of (R)-phenylglycine Amide and 2,2-dimethylpropanal, Conversion into Diamide To a Solution of 9.4 g (38.4 mmol) of aminonitrile in 50 ml of dichloromethane was added, at approx. –10° C., 56 ml of concentrated H$_2$SO$_4$ at such a rate that the temperature remained between –10 and 0° C. Next, the mixture was stirred for 16 hours at 20–25° C. The mixture was poured onto ice, neutralised with 25% aqueous NH$_3$, and extracted with 3×200 ml of ethyl acetate. The combined ethyl acetate layers were dried on MgSO$_4$, filtered and, after concentration by evaporation, 9.5 g of (R,S)-diamide (36.1 mmol, 94%) was obtained as a white solid.

$^1$H NMR (CDCl$_3$): 0.87 (s, 9H, tBu), 2.46 (broad s, 1H, NH), 2.53 (broad s, 1H, CH), 4.08 (s, 1H, CH), 6.35 (broad s, 1H, CONH) 6.40 (broad s, 2H, CONH$_2$), 6.51 (broad s, 1H, CONH) 7.15–7.40 (m, 5H, Ar).

Example V
Hydrogenolysis of the Amino Diamide of (R)-phenylglycine Amide and 2,2-dimethylpropanal: Synthesis of (S)-2-amino-3.3-dimethylbutane Amide.

9.0 g (36.7 mmol) of amino diamide was dissolved in 250 ml of 96% ethanol, after which 0.5 g of 10% Pd/C was added. The mixture was hydrogenated for 20 hours at 0.2 MPa H$_2$ and 20–25° C. After removal of the Pd/C by means of filtration through celite, the solution was concentrated by evaporation at reduced pressure. The crude reaction mixture was purified by means of column chromatography (SiO$_2$, dichloromethane/methanol 9:1). After evaporation of organic solvents 2.2 g (46%) of (S)-2-amino-3,3-dimethylbutane amide was obtained as a solid.

$^1$H NMR (CDCl$_3$): 0.96 (s, 9H, tBu), 1.48 (broad s, 2H NH$_2$), 3.07 (s, 1H, CH), 5.49 (broad s, 1H, CONH) 6.50 (broad s, 1H, CONH).

Example VI
Hydrolysis of (S)-2-amino-3,3-dimethylbutane Amide: Synthesis of (S)-2-amino-3,3-dimethylbutane Acid ((S)-t-leucine).

2.0 g (15.4 mmol) of (S)-2-amino-3,3-dimethylbutane amide in 500 ml of 6N HCl was heated at 100° C. for 24 hours. After cooling to 20–25° C., the mixture was transferred to a Dowex 50 Wx8 column in the NH$_4^+$ form. The column was washed with 250 ml of water and then eluted with approx. 400 ml of 10% aqueous NH$_3$. After evaporation and drying 1.7 g (86%) of (S)-2-amino-3,3-dimethylbutane acid ((S)-t-leucine) was obtained.

$^1$H NMR (D$_2$O): 1.06 (s, 9H, tBu), 3.44 (s, 1H, CH).

Example VII
Synthesis of the Schiff Base of (R)-phenylglycine Amide and 3,3-dimethyl-2-butanone.

To 7.5 g (50 mmol) of (R)-phenylglycine amide were successively added 10.0 g (100 mmol) of 3,3-dimethyl-2-butanone, 40 ml of toluene, 50 ml of cyclohexane and 0.1 g (0.53 mmol) of p-toluene sulphonic acid. The mixture was heated with stirring to reflux (approx. 90° C.). The water formed was collected during the reaction by 4 Å sieves in a soxhlett apparatus. After approx. 48 hours the solution was concentrated by evaporation at reduced pressure. 11.2 g (48.2 mmol, 97%) of the Schiff base was obtained as a white solid, which was utilised as such, without further purification, in the next step.

$^1$H NMR (DMSO-d$_6$): 1.15 (s, 9H, t-Bu), 1.75 (s, 3H, Me), 4.85 (s, 1H, α-H), 7.2–7.4 (m, 5H-arom.)

Example VIII
Reduction of the Schiff Base of (R)-phenylglycine Amide and 3,3-dimethyl-2-butanone with Pt/C and H$_2$ 11.2 g (48.2 mmol) of the Schiff base of (R)-phenylglycine amide and 3,3-dimethylbutanone were dissolved in 100 ml of absolute ethanol whereupon 0.2 g of 5% Pt/C was added. The mixture was hydrogenated for 5 hours at 5 bar H$_2$ and 20° C. On removal of the Pt/C through filtration, the solution was concentrated through evaporation at reduced pressure. The yellow oil obtained was dissolved in 100 ml of ethyl acetate and washed with 2×20 ml of water. After drying on MgSO$_4$, the solution was concentrated through evaporation and was then crystallised from 90 ml of hexane. The solid was filtered, washed with 2×10 ml of hexane and dried to constant weight.

Yield: 6.6 g (57% based on (R)-phenylglycine amide). $^1$H NMR revealed only one stereoisomer (R,S).

1H-NMR (CDCl$_3$): 0.9 (s, 9H, tBu); 1.0 (d, 3H, Me), 2.35 (q, 1H, CHN), 4.25 (s, 1H, αH), 5.6–5.8 (s, 1H, NH), 7.25–7.40 (m, 5H, ar).

Example IX
Reduction of the Schiff Base of (R)-phenylglycine Amide and 3,3-dimethyl-2-butanone with Raney-N$_1$ and H$_2$ 4.0 g (1.7.2 mmol) of the Schiff base of (R)-phenylglycine amide and 3,3-dimethyl-2-butanone were dissolved in 50 ml of absolute ethanol, after which 5 g of wet Raney-Ni (previously washed with 3×30 ml of absolute ethanol) was added. Next, the mixture was hydrogenated with 0.1 MPa H$_2$. The conversion was monitored over time. Conversion was virtually complete after approx. 7 days. The catalyst was removed by filtration and the filtrate was concentrated by evaporation at reduced pressure. The resulting oil was crystallized from hexane to give the amine as a single diastereomer.

Yield: 2.6 g (64% based on (R)-phenylglycine amide). $^1$H NMR: identical as in example VIII.

Example X
Hydrogenolysis of Amino Amide Obtained in Example VIII; Synthesis of (S)-3,3-dimethyl-2-butylamine.HCl 6.6 g (28.2 mmol) amino-amide was dissolved in 100 ml of absolute ethanol whereupon 0.3 g of 10% Pd/C was added. The mixture was hydrogenated for 20–24 hours at 0.5 MPa H$_2$ and 50° C. On cooling and filtration of the Pd/C through Celite, 3 ml of 37% HCl was added. At that point the pH of the mixture was approx. 3.5. Next, the solution was concentrated by evaporation at reduced pressure and the oil obtained was combined with 50 ml of H$_2$O. The water layer was subsequently extracted with 4×25 ml of ethyl acetate in order to remove phenylacetamide. Next, the water layer was concentrated by evaporation and remaining water was removed from the residue by adding 2×30 ml of absolute ethanol followed by distillation. The residue was then crystallised from 50 ml of ethyl acetate.

The solid was filtered, washed with 10 ml of ethyl acetate and dried to constant weight.

3.6 g (26.2 mmol, 93.3%) of (S)-3,3-dimethyl-2-butylamine. HCl was obtained. The rotation of the product indicated that the S-isomer had formed.

The enantiomeric excess was determined through chiral HPLC: e.e.(S)=99%.

$^1$H NMR (DMSO-d$_6$): 0.95 (s, 9H, tBu), 1.15 (d, 3H, Me), 2.95 (q, 1H, CHN), 8.0 (broad, 3H, NH$_3$Cl).

Example XI
Synthesis of the Schiff Base of (R)-phenylglycine Amide and Isobutyraldehyde To 7.5 g (50 mmol) of (R)-phenylglycine amide in 100 ml of dichloromethane were added 5.4 g (50 mmol) of isobutyraldehyde and 0.7 g of 4A sieves. The mixture was stirred for 4 hours at 20–25° C. After filtration, the solution was concentrated by evaporation.

10.8 g (45.0 mmol, 95%) of the Schiff base of (R)-phenylglycine amide and isobutyraldehyde was obtained in the form of a white solid.

$^1$H NMR (CDCl$_3$): 1.06 (m, 6H), 2.46 (m, 1H), 4.67 (s, 1H), 5.68 (broad s, 1H), (bs, 1H), 7.21–7.37 (m, 5H), 7.60 (d, 1H, α-H).

Example XII
Allylation of the Schiff Base of (R)-phenylglycine Amide and Isobutyraldehyde To a mixture of 4.8 g (20.0 mmol) of the Schiff base of (R)-phenylglycine amide and isobutyraldehyde and activated Zn (2 eq) in 100 ml of dry THF was added, with stirring, 2.4 g (20 mmol) of allylbromide, whereby an exothermic reaction occurred. The mixture was stirred for 1 hour at 20–25° C., whereupon 100 ml of a saturated solution of NaHCO$_3$ in water was added, followed by addition of 100 ml of ethyl acetate. The ethyl acetate layer was separated and the water layer was again extracted with 100 ml of ethyl acetate. After drying with MgSO$_4$, filtration and concentration by evaporation, 4.3 g of the homoallylamine (15.4 mmol, 77%) was obtained.

$^1$H NMR (CDCl$_3$): 0.72 (d, 3H), 0.85 (d, 3H), 1.87 (m, 2H), 2.17 (m, 1H), 2.37 (m, 1H), 4.25 (s, 1H), 5.03 (s, 1H), 5.07 (d, 1H), 5.76 (m, 1H), 6.02 (broad s, 1H), 7.20–7.34 (m, 6H).

$^1$H NMR revealed only one stereoisomer: (R,R)

Example XIII
Hydrogenation of (R)-phenylglycine Amide-(R)-isopropylhomoallylamine Homoallylamine (3.7 g, 15.0 mmol) obtained as described in example XII was dissolved in MeOH (100 ml). Water (10 ml), acetic acid (2.5 ml), and Pd(10%)/C (0.6 gram) were added successively. The mixture was shaken under pressurized H$_2$ (30 psi) for 18 hours at room temperature. The MeOH was evaporated under reduced pressure. The residue was diluted with water (50 ml) and bacified to pH=10 with 10% aqueous NaOH. The water phase was extracted with CH$_2$Cl$_2$ (3×40 mL). The combined organic phases were dried on MgSO$_4$ and filtered. After evaporation of the CH$_2$Cl$_2$, pentane was added to the residue. Phenylacetamide was removed via filtration. Evaporation of the pentane yields 2-methyl-3-(R)-amino-hexane as a colourless oil (1.1 g, 64%).

The enantiomeric excess was determined through chiral HPLC: e.e.(R)>98%.

$^1$H NMR (CDCl$_3$): δ0.74–0.84 (m, 8H), 0.85–1.40 (m, 8H), 2.38–2.44 (m, 1H).

Example XIV
Oxidative Ozonolysis of (R)-phenylglycine Amide-(R)-isopropylhomoallylamine Homoallylamine (3.14 g, 12.8 mmol) obtained as described in example XII was dissolved in dichloromethane (100 ml). A 2.5 M methanolic NaOH solution (26 ml) was added. The mixture was cooled to −78° C. and ozone was passed through the reaction mixture for 3 hours. The solution turns bright orange. A mixture of water and diethyl ether was added and the mixture was warmed to room temperature. The organic phase was separated and the water layer was extracted with diethyl ether. The combined organic phases were dried over Na$_2$SO$_4$. Filtration and evaporation of the solvent furnished a yellow oil (crude yield: 2.7 gr). The pure product (1.0 g, 31%) was obtained as a pale yellow oil after purification by column chromatography (silica/ethyl acetate).

$^1$H-NMR (CDCl$_3$): 0.75 (d, 3H), 0.91 (d, 3H), 2.10–2.23 (m, 2H), 2.41–2.51 (m, 1H), 3.0 (m, 1H), 3.70 (s, 3H), 4.34 (s, 1H), 7.25–7.37 (m, 5H).

Example XV
Ozonolysis Followed by Reduction of of (R)-phenylglycine Amide-(R)-isopropylhomoallylamine A solution of 1.49 g (6.0 mmol) of the homoallylamine obtained as described in example 12 in dichloromethane (90 ml) and methanol (30 ml) was cooled to −78° C., and treated with ozone. The progress of the reaction was monitored with TLC (Heptane/ethyl acetate 1/1). After nine minutes, no starting material was found. The mixture was purged with nitrogen and 0.55 g NaBH$_4$ was added at once. The mixture was allowed to reach room temperature and 150 ml water was added. The phases were separated. The aqueous phase was extracted with dichloromethane (2×100 ml) and ethyl acetate (50 ml). The combined organic phases were washed with brine (50 ml), dried (Na$_2$SO$_4$), and evaporated. The resulting solid was purified by column chromatography (silicagel, EtOAc) to give the aminoalcohol as a colorless solid (700 mg, 47%).

$^1$H-NMR (CDCl$_3$): 0.75 (d, 3H), 0.91 (d, 3H), 1.25 (m, 1H), 1.60 (m, 1H), 2.0 (m, 1H), 2.6 (m, 1H), 3.7 (m, 2H), 4.4 (s, 1H), 7.2–7.4 (m, 5H).

What is claimed is:

1. Process for the preparation of a diastereomerically enriched compound having formula (1)

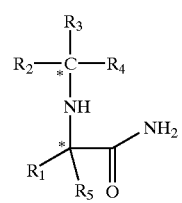

where R$_1$ is a substituted or unsubstituted phenyl group,

R$_2$, R$_3$ and R$_4$ each differ from one another, each R$_2$ and R$_3$ is H, a substituted or unsubstituted (cyclo)alkyl group, alkenyl group, aryl group, cyclic or acyclic heteroalkyl group or heteroaryl group with one or more N, O or S atoms, or is (CH$_2$)$_n$—COR$_6$, where n=0, 1, 2 . . . 6 and R$_6$=OH, a substituted or unsubstituted alkyl group, aryl group, alkoxy group or amino group, R$_4$=CN, H or a substituted or unsubstituted allyl group, and R$_5$ is H or alkyl with 1–6 C atoms, which process comprises reacting a compound of formula (2)

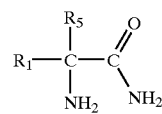

where $R_1$ and $R_5$ have the aforementioned meanings with a compound having formula (3)

(3)

where $R_2$ and $R_3$ have the aforementioned meanings, to obtain the corresponding Schiff base, and treating the Schiff base with a cyanide source, a reducing agent or an allyl organometallic compound to convert said Schiff base into the diastereomerically enriched compound of formula (1).

2. Process according to claim 1 in which $R_4$ is CN and which process further comprises crystallizing the compound of formula (1).

3. Process according to claim 1 wherein $R_4$ is CN and which process further comprises converting said CN into the corresponding acid, amide or ester, and effecting hydrogenolysis to obtain the compound of formula (4).

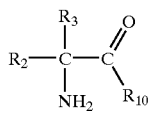

(4)

where $R_{10}$ represents OH, $NH_2$ or alkoxy, and wherein said compound of formula (4) is enantiomerically enriched.

4. Process according to claim 1, wherein $R_4$ is H and which process further comprises effecting hydrogenolysis to obtain the compound of formula (5)

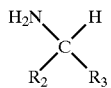

(5)

in which $R_2$ and $R_3$ have the same meanings as in claim 1 except that neither is H, and wherein said compound of formula (5) is enantiomerically enriched.

5. Process according to claim 1, wherein $R_4$ is a substituted or unsubstituted allyl group.

6. Process according to claim 5, which process further comprises converting said substituted or unsubstituted ally group to a

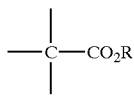

group wherein R is H or alkyl.

7. Process according to claim 5, which process further comprises converting said substituted or unsubstituted allyl to a group of the formula

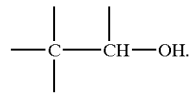

8. Process according to claim 5 which process further comprises hydrogenating said allyl group.

9. A compound having formula (1)

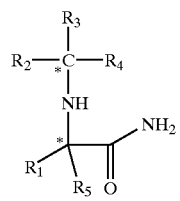

(1)

where $R_1$ is a substituted or unsubstituted phenyl group, $R_2$, $R_3$ and $R_4$ each differ from one another, each $R_2$ and $R_3$ is H, a substituted or unsubstituted (cyclo)alkyl group, alkenyl group, aryl group, cyclic or acyclic heteroalkyl group or heteroaryl group with one or more N, O or S atoms, or is $(CH_2)_n$—$COR_6$, where n=0, 1, 2 . . . 6 and $R_6$=OH, a substituted or unsubstituted alkyl group, aryl group, alkoxy group or amino group, $R_4$=CN, H or a substituted or unsubstituted allyl group, and $R_5$ is H or alkyl with 1–6 C atoms, with proviso that if $R_1$ is unsubstituted phenyl, $R_2$ is $CH(CH_3)_2$, $R_3$ is COOH, and $R_4$ is H, then $R_5$ cannot be H, wherein said compound has a diastereomeric excess greater than 80%.

10. A compound according to claim 9 wherein $R_4$ represents $C(R_7R_7)$—$CHR_7OH$ or $C(R_7R_7)$—$CO_2R_8$ in which each $R_7$ independently is alkyl or aryl, and $R_8$ is alkyl.

11. A compound according to claim 9 with a diastereomeric excess greater than 90%.

12. A compound according to claim 11 with a diastereomeric excess greater than 98%.

13. A compound according to claim 10 with a diastereomeric excess greater than 80%.

14. A compound according to claim 13 with a diastereomeric excess greater than 90%.

15. A compound according to claim 14 with a diastereomeric excess greater than 98%.

16. The process of claim 5 wherein $R_4$ is unsubstituted allyl.

* * * * *